United States Patent [19]

Bradley

[11] 4,076,592

[45] Feb. 28, 1978

[54] METHOD AND APPARATUS FOR TESTING THE EFFECT OF VARIOUS ANTIBIOTICS ON A BACTERIAL SUSPENSION

[76] Inventor: Rex L. Bradley, 6620 Manor Road, Austin, Tex. 78751

[21] Appl. No.: 698,487

[22] Filed: Jun. 21, 1976

[51] Int. Cl.² .............................................. C12K 1/04
[52] U.S. Cl. ............................. 195/103.5 K; 195/127; 23/259
[58] Field of Search ................ 195/103.5 K, 103.5 M, 195/103.5 R, 127, 139, 140; 23/259 R, 259 X

[56] References Cited

U.S. PATENT DOCUMENTS

| 3,832,532 | 8/1974 | Praglin et al. | 195/103.5 K |
| 3,895,661 | 7/1975 | Praglin et al. | 195/127 X |

*Primary Examiner*—Raymond N. Jones
*Assistant Examiner*—Robert J. Warden
*Attorney, Agent, or Firm*—George M. Medwick

[57] ABSTRACT

An apparatus for testing a substance is characterized by a substantially planar base member carrying a reservoir extending lengthwise thereon. A plurality of test zones, each having a chemical substance therein, are carried by the base and are disposed in a side-by-side relationship with each other and in a substantially perpendicular relationship with the reservoir. Each test zone is separated and isolated from the next adjacent test zone by a sidewall of a predetermined height. The test zones are each separated from the reservoir by a barrier having a height less than the height of the sidewall. A clear plastic cover is provided to enclose the reservoir and the test zones so that fluid communication is permitted only between each individual test zone and the reservoir through a clearance space defined between the interior of the cover and the top of the barrier. After introduction of the substance to be tested within the reservoir, the method comprises rotating the testing apparatus a predetermined angular distance about an axis of rotation extending longitudinally through the reservoir to permit the substance to be tested into enter each of the test zones through the defined clearance. The testing apparatus may be rotated in an angular direction opposite to the first angular direction to thereby return the apparatus to its original position and isolate the substance to be tested in each individual test zone.

16 Claims, 5 Drawing Figures

METHOD AND APPARATUS FOR TESTING THE EFFECT OF VARIOUS ANTIBIOTICS ON A BACTERIAL SUSPENSION

BACKGROUND OF THE INVENTION

1. Field of the Invention

This invention relates to apparatus for testing a chemical substance and more particularly, to an apparatus for testing the effect of antibiotics on a bacterial suspension.

2. Description of the Prior Art

The sensitivity of bacterial elements to antibiotics is usually ascertained by observing the reaction between a particular bacterial element and a plurality of chemical substances arranged in predetermined test zones or chambers provided within a testing apparatus. The testing apparatus usually is provided with a transparent covering so the effect of the various chemicals on the particular bacterial element may be easily observed and recorded.

In the prior art, it is common practice to individually apply or introduce the appropriate bacterial element into each of the reagent-containing test zones or chambers provided in a testing apparatus. As examples of one type of such prior art testing apparatus are U.S. Pat. Nos. 3,873,271 (Anderson), 3,829,223 (Hamel), and 3,759,666 (Hill). These mentioned patents utilize the centrifugal force of rotation of a testing apparatus to impel bacterial elements individually placed in a first chamber from that chamber into a radially-outer test chamber. U.S. Pat. No. 3,826,717 (Gilbert), and U.S. Pat. No. 3,936,356 (Janin) describe a second such type of testing apparatus have a substantially planar test vessel again in which the bacterial element to be evaluated is individually placed within the test zones or chambers provided. U.S. Pat. No. 3,854,883 (Montagnon), and U.S. Pat. No. 3,876,377 (Cinqualbre) also disclose testing apparatus having single or plural test zones requiring individual introduction of bacterial elements thereinto.

U.S. Pat. Nos. 3,373,719 (Avakian), 3,476,515 (Johnson), 3,649,464 (Freeman), 3,713,985 (Astle), and 3,728,228 (Duranty) disclose testing apparatus having individual test zones arranged in side-by-side relationship. U.S. Pat. Nos. 3,832,532 and 3,895,661 (both to Praglin) describe testing apparatus in which bacterial elements to be tested are first inserted in a reservoir provided at one end of the testing apparatus. The testing apparatus must then be rotated about a pivot point located at the reservoir end of the testing apparatus to dispose the bacterial elements into a plurality of interconnected distribution lobes. U.S. Pat. Nos. 3,925,166 (Blume) and 3,837,746 (Acker) require the presence of a differential pressure in order to draw the bacterial element to be tested into the appropriate test chambers.

Prior art testing apparatus also is known that requires provision to be made to prevent the dehydration of the bacterial elements after introduction to the testing apparatus. Such provisions usually include an enclosure or the like, disposed as a humidor, in order to maintain the desired humidity conditions for the test.

It is advantageous, therefore, to provide a testing apparatus for testing a substance that has a common reservoir into which the substance to be tested is placed, the reservoir supplying a plurality of individual test zones or chambers so that the time consuming individual introduction process may be avoided. It is also advantageous to avoid the requirement of applying a suction or pressure differential to draw the substance to be tested into the test zones. It is of further advantage to provide an apparatus which permits introduction of the bacterial element into each individual test zone or chamber expeditiously through the provision of a common reservoir and yet prevent intercommunication between the test zones or chambers which may vitiate the test. It is of still further advantage to provide a testing apparatus which does not require centrifugal force to draw the bacterial elements into the test zones, and, therefore, does not require expensive equipment, such as a centrifuge, in order to perform a test on a given bacterial element. It would be of even further advantage to provide a testing apparatus of a construction such that even inadvertent spillage of bacterial elements from the individual test zones or chambers back again into the common reservoir would not compromise the test efficiency. Also advantageous is a testing apparatus which allows access to the individual test zones or chambers without disturbing the other test zones. It is also advantageous to provide a testing apparatus which maintains a predetermined humidity condition within the test zones or chambers, to avoid dehydration of the bacterial elements, without the necessity of an associated humidor arrangement, or the like.

SUMMARY OF THE INVENTION

This invention relates to an apparatus and to a method for testing the effect of antibiotics on bacterial elements. The apparatus includes a substantially planar base having carried thereon or provided therein a predetermined plurality of substantially side-by-side test zones or chambers. Each test zone has a chemical substance therein. Interconnection or intercommunication between the adjacent test zones or chambers is substantially prohibited by upstanding sidewalls disposed between each next adjacent test zone which separate the zones from each other. A reservoir is carried longitudinally across the length of the base substantially perpendicular to each of the test zones and substantially coextensive in length with the plurality of side-by-side test zones. A clear plastic cover is provided over the base, the cover contacting the top of each of the sidewalls and the base.

A barrier is located between the reservoir and each of the individual test zones. The height of the barrier is less than the height of the sidewall, with both heights being measured from a predetermined reference datum, such as a point located within the test zone. Defined between the top of the barrier and the interior of the cover is a clearance space or communication channel which permits fluid communication between the reservoir and each individual test zone. A resealable tab is provided through which introduction of the bacterial element to be tested into the reservoir may be effected. Once the element is introduced into the reservoir, the entire testing apparatus is rotated about an axis of rotation extending through the reservoir so that the bacterial element may pass through the individual clearance spaces or communication channels defined between the barrier and the interior of the cover and enter the individual test zones. Intercommunication between the individual zones is prohibited by the sidewalls. Accidental or inadvertent spillage of reacted bacterial element from the individual test zones back into the reservoir does not jeopardize the validity of test since reintroduction of the tested element to the reservoir does not contaminate the other test zones due to the provision of the barrier.

Provided for convenience is a plurality of peelable and resealable tabs disposed adjacent each individual test zone to permit selective access to an individual test zone to the exclusion of the other test zones. Also provided are suitable means to permit the testing apparatus to be maintained in either a vertical or a horizontal orientation.

BRIEF DESCRIPTION OF THE DRAWINGS

The invention will be more fully understood from the following detailed description of a preferred embodiment thereof taken in connection with the accompanying drawings, in which.

DESCRIPTION OF THE PREFERRED EMBODIMENT

Figure 1:
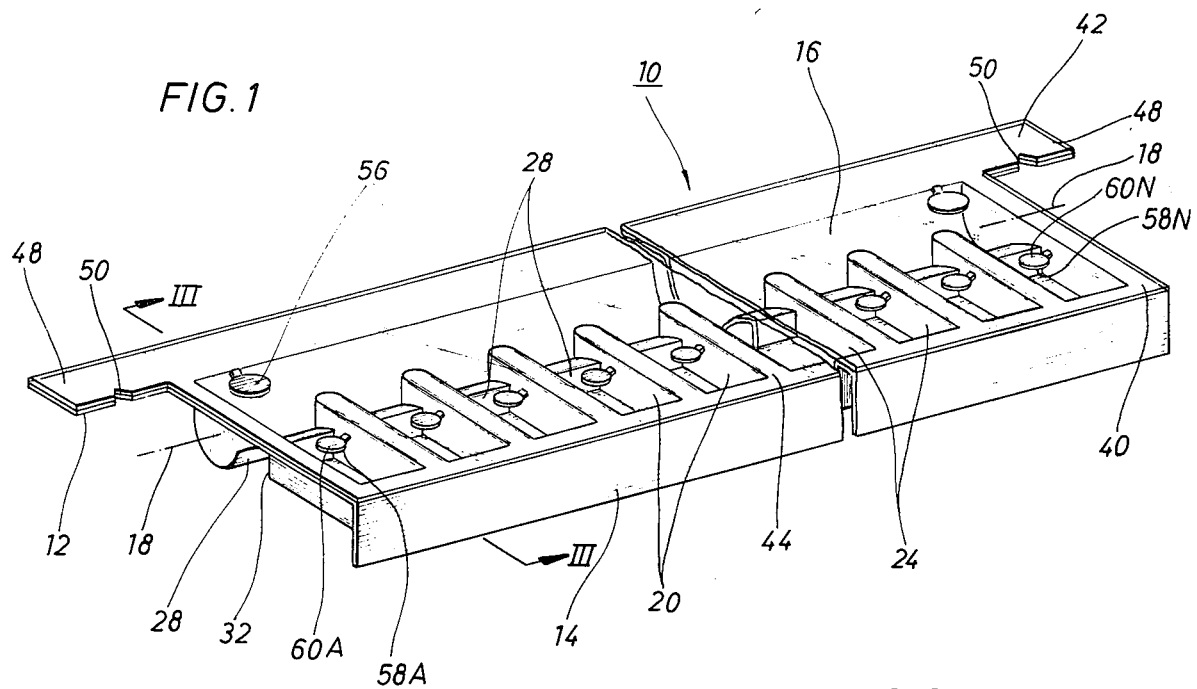
FIG. 1 is a perspective view of an apparatus for testing a substance embodying the teachings of this invention.

Throughout the following description, similar reference numerals refer to similar elements in all figures of the drawings.

Referring to the figures, an apparatus 10 for testing a substance and embodying the teachings of this invention is illustrated. The testing apparatus 10 may, for example, be utilized to test the effect of antibiotics on a bacterial suspension, and comprises a substantially planar base portion 12 fabricated, for example, from a plastic coated paper material on which suitable legends may be printed, although it is understood that other materials may be used. The base 12 may be provided with a leg 14 extending perpendicularly to the base 10. Carried by or disposed within the base 12 in any suitable manner is a reservoir 16. The reservoir 16 is shown as extending substantially the entire length of the testing apparatus 10. The reservoir 16 has an axis 18 extending therethrough and may preferably be formed by depressing the base 12.

A predetermined plurality of N (N being any desired number) side-by-side test zones or chambers 20 are carried by or disposed within the base 12 in any suitable manner. The test zones 20 may be preferably formed as depressions within the base 12. The test zones 20 are disposed so that longitudinal axes 21 extending therethrough are substantially perpendicular to the axis 18 of the reservoir 16. The length of the N side-by-side plurality of test zones 20 is substantially co-extensive with the length of the reservoir 16. Although the test zones 20 are shown to be substantially rectanguloid in volume, any suitable volume may be used. Chemical substances 22 are provided in each of the test zones 20. The chemical substances 22 may be dried chemical reagents known to the art which are hydrated by and react with a suspension of bacterial elements exposed thereto.

Intercommunication between adjacent test zones 20 is prohibited by upstanding sidewalls 24 extending substantially vertically from the bottom 26 of the test zone 20. The sidewalls 24 serve to isolate adjacent test zones 20. The height of the sidewall 24, as measured from, for example, a predetermined point 27 disposed on the bottom 26 of the zone 20, is indicated diagrammatically in FIG. 3 as the vertical distance 30. Of course, any suitable reference datum within the test zone may be used by which to indicate the height of the sidewall 24. For example, the deepest point in a test zone, if the zones were, for example, circular depressions in cross section, may be a convenient reference datum.

Carried by or disposed within the base 12 and disposed intermediate between the reservoir 16 and each of the test zones 20 is a barrier 28. The barrier 28 may be provided in any suitable manner. For example, the barrier 28 is shown as being formed by pressing the base 12 to form a wall portion 32 extending perpendicularly to the sidewall 24 and extending upwardly from the bottom of the test zone 20 for a second vertical distance 34 (measured relative to the same datum as the distance 30, here, the point 27). The distance 34 is, as seen, less than the distance 30. A curved surface 36 leads from the top of the wall 32 of the barrier 28 toward the reservoir 16, all points on the curved surface 36 being below the top of the sidewalls 24.

A substantially planar cover 40 is fabricated preferably of a clear, transparent, non-reactive plastic material known to those skilled in this art. The cover 40 is disposed so as to contact the base 12 (as at 42) and the top of each sidewall 24 (as at 44). The cover 40 may be affixed by any suitable means, such as glueing or heat sealing. A clearance space or communication channel 46 is defined between the curved surface 36 of the barrier 32 and the interior surface of the cover 40. Thus, each of the test zones 20 is appreciated as being adjacent to and in fluid communication with the reservoir 16 through the clearance space 46.

Figure 2:
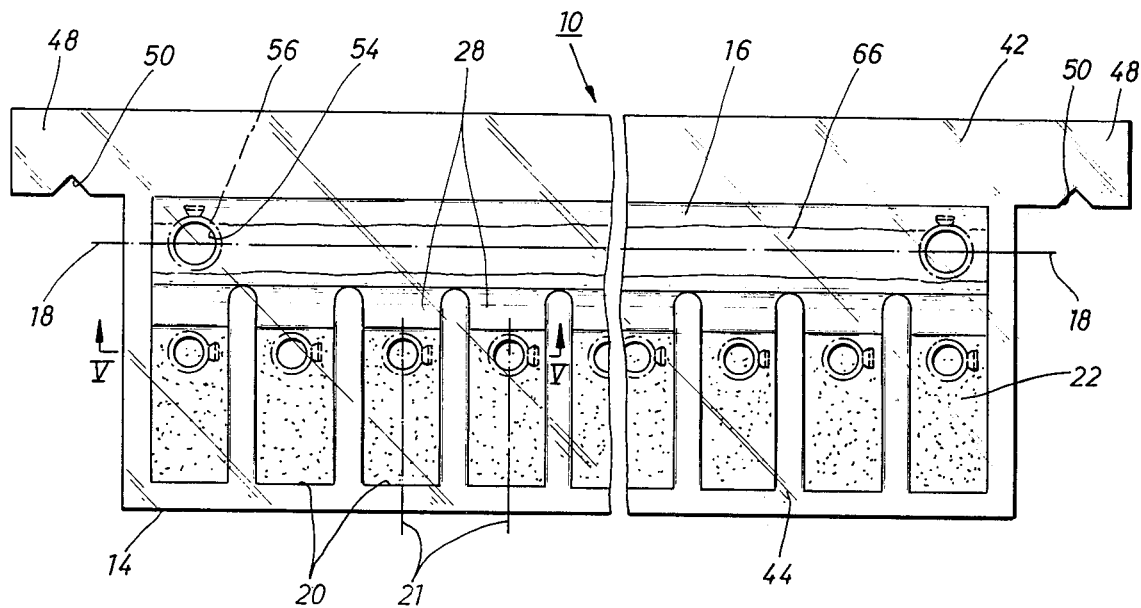
FIG. 2 is a plan view of the apparatus of FIG. 1 for testing a substance embodying the teachings of this invention.
Figure 5:
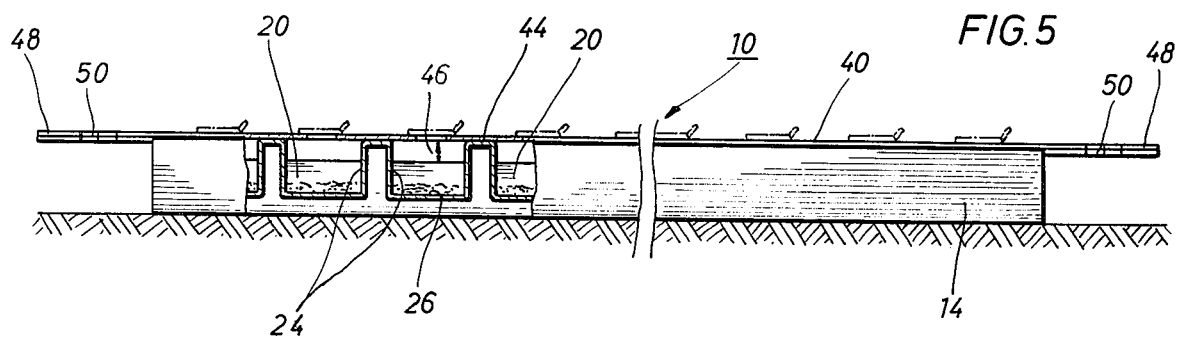

It is appreciated that provision of the base 12 and the cover 40 defines a plurality of substantially closed test zones or chambers 20, each test zone 20 communicable with the adjacent reservoir 16 through the clearance 46 and yet isolated and separated from the adjacent test zone 20 by the sidewall 24. Extensions 48 are provided on the base 12 (FIGS. 1, 2, and 5) and have disposed therein suspending openings or suspending notches 50 which comprises means for supporting the test apparatus 10 so as to dispose the base 12 substantially perpendicular to a predetermined datum, for reasons which will become apparent herein.

An opening 54 is provided through the cover 40 above the reservoir 16. A pull tab 56 is resealably affixed to the cover 40 adjacent the periphery of the opening 54. The opening 54 and the tab 56 comprises reservoir inlet means disposed in the cover 40 for permitting the introduction of the substance to be tested into the reservoir 16. Conveniently, the substance to be tested may be a hydrous bacterial suspension to hydrate any dehydrated chemical reagents 22 disposed in the test zones 20. It is appreciated that since the tab 56 is resealed after the introduction of the hydrous bacterial suspension, moisture is maintained within the testing apparatus 10 to provide a satisfactory humidity condition therein. A plurality of openings 58A-N, (where N equals the number of test zones 20 defined within the testing apparatus 10), are disposed in the cover 40 adjacent each of the test zones 20. Suitable covers or tabs 60A–N are resealably affixed to the cover 40 adjacent the periphery of each of the openings 58A–N. It is appreciated that the plurality of openings 58A–N and the tabs 60A–N comprises test zone inlet means for introducing a test member (not shown) or otherwise communicating with a selected one of the test zones 20 without disturbing other of the test zones 20. This arrangement provides access to each of the test zones for the introduction of selected additional reagents which may be required or desired in an analysis of the bacterial suspension.

Figure 3:
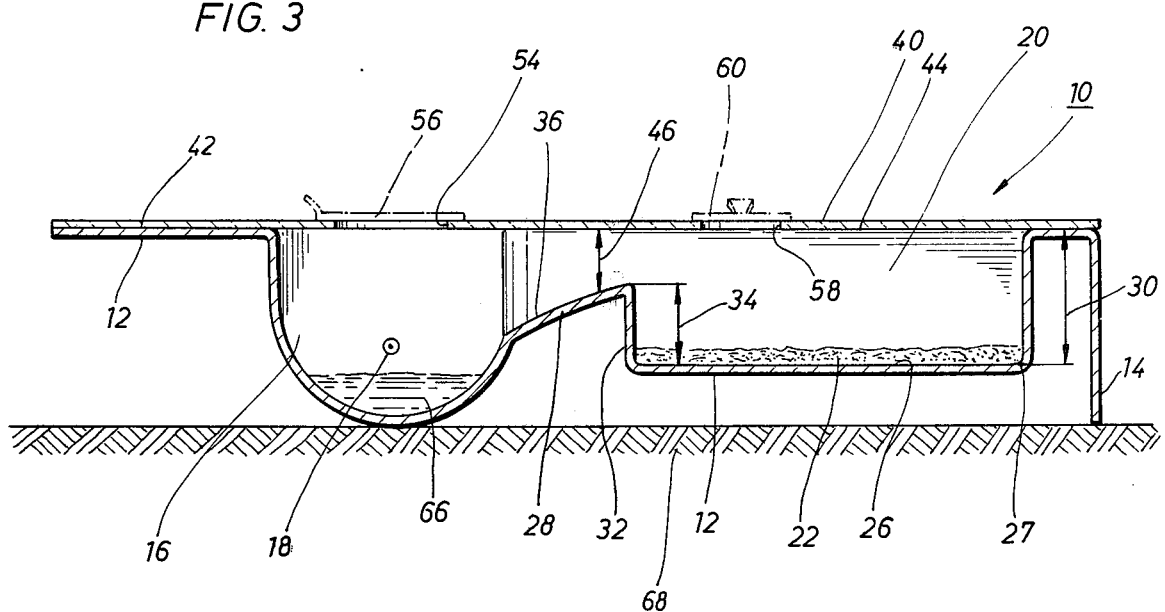
FIG. 3 is an expanded sectional view, taken along section lines III—III of FIG. 1, illustrating an apparatus for testing a substance embodying the teachings of this invention.
Figure 4:
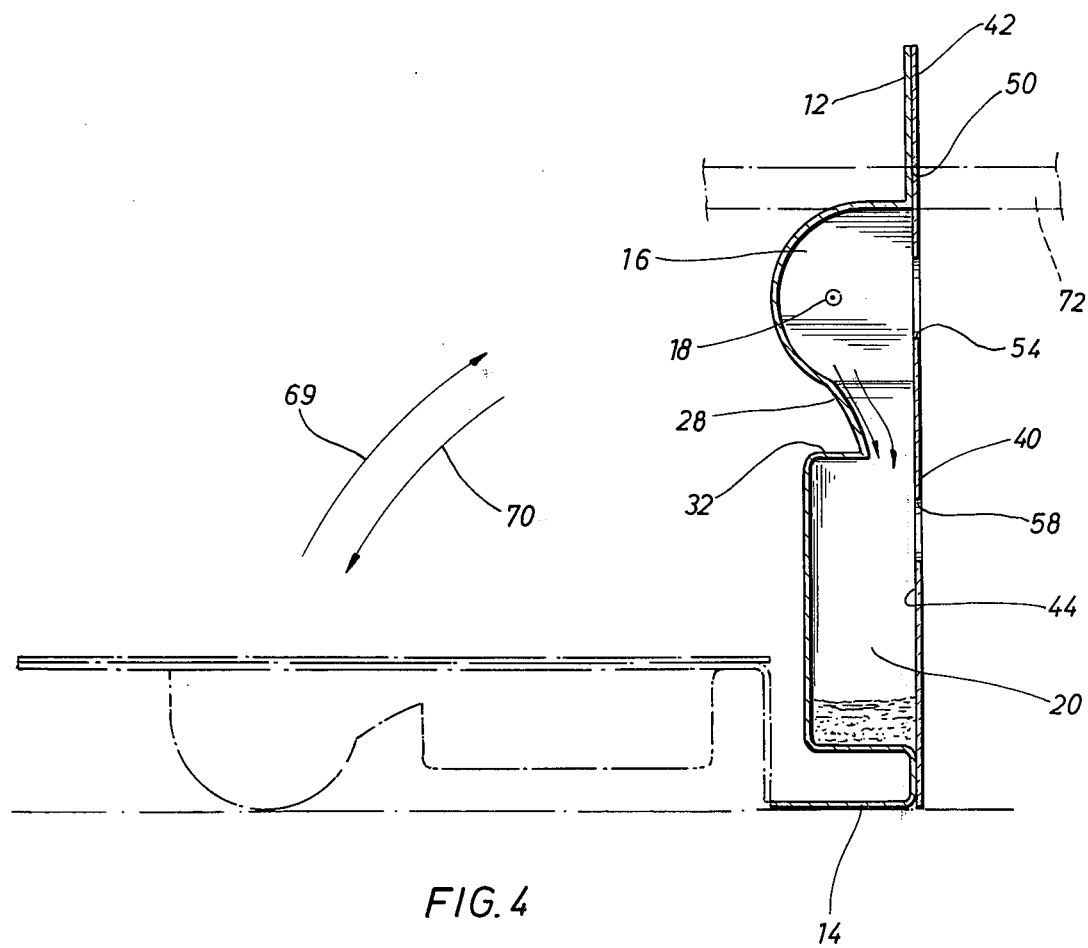
FIG. 4 is a view similar to FIG. 3 which, when taken in connection with FIG. 3, illustrates the practice of the steps embodying the testing method discosed by this invention; and, FIG. 5 is a partial sectional view, taken along section lines V—V of FIG. 2, illustrating an apparatus for testing a substance embodying the teachings of this invention.

With reference to FIGS. 3 and 4, the tab 56 adjacent the periphery of the opening 54 may be removed so that a suitable bacterial element, illustrated by numeral 66, may be introduced within the reservoir 16. During the introduction of the bacterial element (preferrably a liquid bacterial suspension) into the reservoir 16, it is preferred to dispose the apparatus 10 along a level surface 68. The leg 14 assists in maintaining the testing apparatus in the stable horizontal position shown in FIG. 3. It is noted that such disposition is not necessarily required. Once a predetermined amount of bacterial element 66 in liquid suspension is introduced within the reservoir 16 and the cover tab 56 reaffixed, the testing apparatus 10 is rotated in a predetermined angular direction 69 from the first position (shown in FIG. 3) to a second position (shown in FIG. 4). That is, the apparatus 10 is rotated in a first angular direction about an axis of rotation parallel to (or coincident with) the axis 18 of the reservoir 16. Such rotation causes the bacterial element 66 disposed within the reservoir 16 to respond to gravity and to flow through the clearance space 46 into the individual test zones 20. Upon introduction of the bacterial element within the individual test zones 20, the apparatus 10 is rotated in a second angular direction 70, opposed to the first angular direction 69, back to the first position (FIG. 3). In the alternative, however, if it is desired that the apparatus 10 be maintained substantially perpendicular to the level surface 68, the leg 14 may be left in contact with the surface 68 to provide means to support the testing apparatus 10. As a further alternative, the suspending openings or notches 50 provided on the extensions 48 of the base 12 may be conveniently supported suitable support rack 72, or the like.

It may thus be appreciated from the foregoing that an apparatus and method embodying the teachings of this invention provides a simple and efficient manner of expeditiously introducing a bacterial element to be tested to a plurality of test chambers. It will also be appreciated that intercommunication between the adjacent test zones or chambers is effectively prohibited by the sidewalls. Further, accidental or inadvertent spillage of the exposed bacterial element from the test zones or chambers, back through the clearance space and back into the reservoir 16, does not deleteriously affect any chemical reactions occurring in other of the test zones or chambers unless, after that spillage, the apparatus 10 is again rotated so as to reintroduce fluid then within the common reservoir back into the individual test zones. It is appreciated that centrifugal force is not required to initiate a test using a testing apparatus embodying the teachings of this invention. It is also appreciated that through the provision of the individual openings 58 and tabs 60, access to any selected one of the test zones or chambers 20 to the exclusion of other of the test zones or chambers 20 may be effected. Removal of the tab 60 permits insertion of a suitable test member of the like into the pre-selected individual one of the test zones or chambers without disturbing the chemical reactions occurring in any other of the test zones or chambers. Also, a testing apparatus 10 embodying the teachings of this invention is seen to maintain the humidity condition within the test zones after the introduction of the hydrous bacterial suspension at a predetermined condition, without the necessity of a humidor, or the like.

It is, therefore, appreciated that an apparatus embodying the teachings of this invention and a method utilizing the steps herein above discussed provides a simple, efficient and effective manner of testing a bacterial element with chemical substances disposed in a plurality of test chambers.

I claim as my invention:

1. Apparatus for testing a substance comprising:
   a substantially planar base;
   a reservoir carried by said base and having an axis extending therethrough;
   a plurality of side-by-side test zones carried by said base, each test zone having a chemical substance therein, each of said test zones being separated from its next adjacent test zone by a sidewall, each sidewall extending upwardly above a predetermined point in each test zone for a first predetermined distance, each of said test zones being adjacent to and in fluid communication with said reservoir; and,
   a barrier disposed between each of said test zones and said reservoir, said barrier extending upwardly above said predetermined point in each test zone for a second predetermined distance less than said first predetermined distance;
   said test zones, reservoir and barrier being cooperably arranged so that a substance to be tested disposed in said reservoir may be introduced therefrom over said barrier and into each of said test zones by the angular movement of said base about said axis extending through said reservoir.

2. Apparatus according to claim 1, further comprising:
   a substantially planar cover disposed over said base and contacting the top of each of said sidewalls.

3. Apparatus according to claim 2, further comprising:
   reservoir inlet means disposed in said cover for permitting introduction into said reservoir of a liquid medium having a substance to be tested disposed therein.

4. Apparatus according to claim 3, wherein
   said reservoir inlet means comprises an opening disposed in said cover, and,
   a tab resealably affixed to said cover about a periphery of said opening.

5. Apparatus according to claim 2, further comprising:
   test zone inlet means disposed in said cover for inserting a member into a predetermined one of said test zones.

6. Apparatus according to claim 5, wherein
   said test zone inlet means comprises a plurality of openings disposed in said cover, one opening being proximate to each of said test zones, and,
   a plurality of tabs, one tab being resealably affixed to said cover about the periphery of each of said openings.

7. Apparatus according to claim 2, and further comprising:
   reservoir inlet means disposed in said cover for permitting introduction into said reservoir of a liquid medium having a substance to be tested disposed therein; and,
   test zone inlet means disposed in said cover for inserting a member into a predetermined one of said test zones.

8. Apparatus according to claim 7, wherein
   said reservoir inlet means comprises an opening disposed in said cover and a tab resealably affixed to said cover about the periphery of said opening, and wherein
   said test zone inlet means comprises a plurality of openings disposed in said cover, one opening being proximate to each of said test zones, and a plurality of tabs, one tab being resealably affixed to said cover about the periphery of each of said openings.

9. Apparatus according to claim 2, wherein
   said cover is fabricated from a transparent material.

10. Apparatus according to claim 2, further comprising:
    support means disposed on said base for supporting said base in a substantially vertical position relative to a predetermined datum.

11. Apparatus according to claim 10, wherein
    said support means comprises first and second extensions integral with said base; and,
    said first and said second extensions each having a suspending notch provided therein.

12. Apparatus according to claim 1, wherein
    said barrier has a curved surface thereon disposed between said test zone and said reservoir, all points on said surface being vertically above said predetermined point for distances less than said second predetermined distance.

13. A method for a testing a an antibiotic substance comprising of steps of:
    inserting a substance to be tested in a reservoir disposed in a testing apparatus while the testing apparatus is in a first position;
    rotating said testing apparatus about an axis extending through said reservoir a predetermined angular amount in a first predetermined angular direction to introduce said substance to be tested from said reservoir into a plurality of side-by-side test zones each having an antibiotic substance therein;
    inserting a test member into one of said plurality of test zones in said test apparatus independently of the other of said zones;
    retracting said test member from said one of said zones;
    and observing the reaction of said antibiotic substance within said test zone.

14. The method of claim 13, further comprising the step of:
    rotating said test apparatus a predetermined angular amount in an angular direction opposite said first predetermined angular direction to return the testing apparatus to the first position.

15. The method of claim 13 further comprising the step of:
    suspending said test apparatus to dispose said test apparatus substantially perpendicular to a predetermined datum.

16. The method according to claim 13, further comprising the steps of:
    opening a tab provided in said test apparatus proximate to one of said test zones prior to the inserting of said test member thereinto; and,
    closing said tab after said test member is retracted from said one of said test zones.